(12) United States Patent
France et al.

(10) Patent No.: US 7,469,703 B2
(45) Date of Patent: Dec. 30, 2008

(54) STAIN-REMOVAL BRUSH

(75) Inventors: Paul Amaat Raymond Gerard France, West Chester, OH (US); Bradley Wayne Daubenspeck, West Chester, OH (US); Linda Shumansky Girard, Union, KY (US); Stephen Allen Jacobs, Fairfield, OH (US); Roberto Mastrigli, Etterbeek (BE); Neil Anthony Litten, Egham (GB); Graham John Boyd, Beijing (CN); Gregory Clegg Spooner, Hong Kong (CN)

(73) Assignee: The Procter & Gamble Company, Cincinnati, OH (US)

( * ) Notice: Subject to any disclaimer, the term of this patent is extended or adjusted under 35 U.S.C. 154(b) by 614 days.

(21) Appl. No.: 10/762,877

(22) Filed: Jan. 22, 2004

(65) Prior Publication Data

US 2005/0199265 A1     Sep. 15, 2005

Related U.S. Application Data

(63) Continuation-in-part of application No. 10/659,868, filed on Sep. 11, 2003, now Pat. No. 7,258,747.

(60) Provisional application No. 60/409,861, filed on Sep. 11, 2002, provisional application No. 60/441,689, filed on Jan. 22, 2003.

(51) Int. Cl.
*B08B 7/04* (2006.01)
(52) U.S. Cl. ................ 134/25.2; 134/25.4; 15/22.1; 15/22.2
(58) Field of Classification Search ............... 68/213; 15/21.1, 22.1, 29; 8/148
See application file for complete search history.

(56) References Cited

U.S. PATENT DOCUMENTS

| 1,374,772 | A | * | 4/1921 | Smith | 15/24 |
| 2,164,965 | A | * | 7/1939 | Traube | 68/214 |
| 2,588,000 | A | * | 3/1952 | Hines | 15/320 |
| 2,756,446 | A | * | 7/1956 | Chittum | 15/29 |
| 2,911,660 | A | * | 11/1959 | Klemas et al. | 15/28 |
| 3,055,031 | A | | 9/1962 | Raclin | |
| 3,289,239 | A | * | 12/1966 | Diebold et al. | 15/320 |

(Continued)

FOREIGN PATENT DOCUMENTS

DE       3 615 918 A1    11/1987

(Continued)

OTHER PUBLICATIONS

Whitey Pika UW-8000 Handy Type Ultrasonic Wave Point Stain Remover from Kumazaki-Aim Company—Dec. 2003.

(Continued)

*Primary Examiner*—Frankie L Stinson
(74) *Attorney, Agent, or Firm*—Julia A. Glazer; Kim William Zerby; Steven W. Miller

(57) ABSTRACT

An motorized stain-removal brush is provided. A method of using motorized stain-removal brush for cleaning inanimate surfaces is also provided. The motorized stain-removal brush includes a handle having a motor disposed therein, a head having a longitudinal axis, and a neck disposed between the handle and the head. Bristle holders are associated with the head. The motor is operatively connected to the bristle holder.

22 Claims, 10 Drawing Sheets

U.S. PATENT DOCUMENTS

| | | | |
|---|---|---|---|
| 3,443,272 A * | 5/1969 | Petri et al. ............... | 15/29 |
| 4,097,953 A * | 7/1978 | McKinney et al. ......... | 15/320 |
| 4,177,532 A | 12/1979 | Azuma | |
| 4,223,418 A | 9/1980 | Pedrini | |
| 4,279,051 A * | 7/1981 | Malcolm ................ | 15/29 |
| 4,397,056 A * | 8/1983 | Miller .................... | 15/22.1 |
| 4,574,414 A | 3/1986 | Zhadanov | |
| 4,841,590 A | 6/1989 | Terry et al. | |
| 5,146,642 A * | 9/1992 | Mank et al. ............ | 15/24 |
| 5,153,962 A | 10/1992 | Ritter | |
| 5,156,634 A | 10/1992 | Yang | |
| 5,333,337 A * | 8/1994 | Markley .................. | 15/29 |
| 5,345,640 A | 9/1994 | Goss | |
| 5,353,461 A | 10/1994 | Enriquez | |
| 5,367,740 A * | 11/1994 | McCray ................... | 15/320 |
| 5,418,996 A | 5/1995 | Chen | |
| 5,423,102 A * | 6/1995 | Madison ................ | 15/22.2 |
| 5,499,420 A * | 3/1996 | Boland ................... | 15/22.1 |
| 5,524,312 A | 6/1996 | Tan et al. | |
| 5,701,625 A | 12/1997 | Siman | |
| 5,707,163 A | 1/1998 | Gregory | |
| 5,718,014 A | 2/1998 | DeBlois et al. | |
| 5,864,911 A | 2/1999 | Arnoux et al. | |
| 5,870,790 A | 2/1999 | Root et al. | |
| 5,875,509 A * | 3/1999 | Facca ..................... | 15/120.1 |
| 5,950,268 A * | 9/1999 | Murphy et al. .......... | 15/28 |
| 5,956,792 A | 9/1999 | Gutelius et al. | |
| 5,964,003 A * | 10/1999 | Rogers .................... | 15/98 |
| 5,978,999 A * | 11/1999 | deBlois et al. ........... | 15/22.1 |
| 6,000,083 A | 12/1999 | Blaustein et al. | |
| 6,000,626 A | 12/1999 | Futo et al. | |
| 6,020,300 A | 2/2000 | Tcheou et al. | |
| 6,032,313 A | 3/2000 | Tsang | |
| 6,059,475 A | 5/2000 | Jafarmadar | |
| 6,170,107 B1 | 1/2001 | George et al. | |
| 6,170,108 B1 | 1/2001 | Knight | |
| 6,178,579 B1 | 1/2001 | Blaustein et al. | |
| 6,189,693 B1 | 2/2001 | Blaustein et al. | |
| 6,210,064 B1 | 4/2001 | White et al. | |
| 6,233,771 B1 * | 5/2001 | Hortel et al. ............ | 8/150 |
| 6,253,405 B1 | 7/2001 | Gutelius et al. | |
| 6,295,681 B1 | 10/2001 | Dolah | |
| 6,311,837 B1 | 11/2001 | Blaustein et al. | |
| 6,499,174 B2 | 12/2002 | Henrie | |
| 6,647,577 B2 * | 11/2003 | Tam ........................ | 15/28 |
| 6,832,543 B2 * | 12/2004 | Siano et al. ............. | 99/340 |
| 2002/0112741 A1 | 8/2002 | Pieroni et al. | |
| 2002/0129835 A1 | 9/2002 | Pieroni et al. | |
| 2003/0084524 A1 | 5/2003 | Blaustein et al. | |
| 2003/0084525 A1 | 5/2003 | Blaustein et al. | |
| 2003/0084526 A1 | 5/2003 | Brown et al. | |
| 2003/0084528 A1 | 5/2003 | Chan et al. | |
| 2003/0126699 A1 | 7/2003 | Blaustein et al. | |

FOREIGN PATENT DOCUMENTS

| | | |
|---|---|---|
| JP | 05-146313 | 6/1993 |
| JP | 11-032971 | 2/1999 |
| WO | WO 02/49497 A2 | 6/2002 |

OTHER PUBLICATIONS

Bissell-to-Go Spot Scrubber from www.greenfieldonline.com—on or about Nov. 12, 2003.

* cited by examiner

STAIN-REMOVAL BRUSH

CROSS REFERENCE TO RELATED APPLICATIONS

This application claims the benefit of U.S. Provisional Application Ser. No. 60/441,689 filed Jan. 22, 2003, and is a continuation-in-part of U.S. Ser. No. 10/659,868 filed on Sep. 11, 2003, now U.S. Pat. No. 7,258,747, which claims the benefit of U.S. Provisional Application Ser. No. 60/409,861, filed Sep. 11, 2002.

FIELD

The present invention relates to stain-removal brushes for fabrics or inanimate hard surfaces. More specifically, the invention relates to electric stain-removal brushes for fabrics or inanimate hard surfaces.

BACKGROUND

The art is replete with techniques for transforming the rotational output of a motor or other electromotive power source into desired brushing motions. Many techniques include a shaft as a component of the drive train. The shaft may rotate, oscillate, or reciprocate. The shaft is coupled to a bristle holder. Most often, the bristle holder is driven by the shaft in a rotating or oscillating manner about an axis which is normal to the longitudinal axis of the shaft.

Such motorized brushes typically provide only a non-angled or non-tilted brush head. While those brush heads are beneficial, it is believed that a tilted brush head with a defined cleaning efficiency angle on motorized brushes can provide superior cleaning action. Further, there is believed to be an optimum oscillation frequency range and bristle holder diameter.

SUMMARY

The present invention is directed to an article of commerce and a method of cleaning an inanimate surface. The article of commerce comprises
a motorized stain-removal brush, wherein the motorized stain-removal brush comprises
i) a handle having a motor disposed therein;
ii) a head having a longitudinal axis;
iii) a neck disposed between the handle and the head;
iv) a bristle holder associated with the head which oscillates or rotates and has a cleaning efficiency angle of between 0 and 100 degrees;
v) a set of bristles or a foam structure associated with the bristle holder; wherein the motor is operatively connected to the bristle holder. The article of commerce may also include a set of instructions in association with the motorized stain-removal brush, wherein the instructions direct a user of the motorized stain-removal brush to put a solution in contact with the inanimate surface and use the motorized stain-removal brush to brush the solution on the inanimate surface.
The present invention is further directed to a method of cleaning an inanimate surface comprising:
a) providing a motorized stain-removal brush having a cleaning efficiency angle of from between about 0 degrees to 100 degrees, wherein the motorized stain-removal brush comprises:
i) a handle having a motor disposed therein;
ii) a head having a longitudinal axis;
iii) a neck disposed between the handle and the head;
iv) a bristle holder associated with the head which oscillates;
b) a set of bristles associated with the bristle holder wherein the motor is operatively connected to bristle holder. A solution is placed in contact with an inanimate surface. The surface is then contacted with the stain-removal brush so as to brush the solution on the inanimate surface.

These and other features, aspects, and advantages of the present invention will become evident to those skilled in the art from a reading of the present disclosure.

BRIEF DESCRIPTION OF THE DRAWINGS

It is believed that the present invention will be better understood from the following description taken in conjunction with the accompanying drawings in which.

DETAILED DESCRIPTION

Reference will now be made in detail to various embodiments of the present invention, examples of which are illustrated in the accompanying drawings wherein like numerals indicate the same elements throughout the views. All percentages, ratios and proportions herein are on a weight basis unless otherwise indicated.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

As used herein, "inanimate surface" means a surface that does not make up a part of a living organism (e.g., does not include teeth). Examples of inanimate surfaces include, but are not limited to, fabrics and hard surfaces.

As used herein, "stain-removal brush" means a brush for cleaning an inanimate surface.

As used herein, "motorized" and "electric" are used interchangeably to refer to the use of power source to activate the stain-removal brush. Sources of power include but are not limited to batteries, plug-in electrical sources such as commonly used 110V and 220V current, solar power, and the like.

A. Stain-removal brush

As will be appreciated, the present invention is directed to electric stain-removal brushes (including electric stain-removal brushes having replaceable heads) and electric stain-removal brush heads having moving bristle holders. The bristle holder rotates or oscillates or reciprocates and translates, or performs any other non-rotational or oscillatory motion. Herein, the term "rotate" is intended to refer to a unidirectional angular motion (e.g., a constant clockwise motion) while the term "oscillate" is intended to refer to vibratory angular motion (e.g., repeated cycles of clockwise rotation and counter clockwise rotation). Vibration is any periodic movement having repeated cycles. Vibratory motion can have one or more frequencies and amplitudes. Vibratory motion that is substantially linear is referred to herein as a reciprocating motion.

Figure 1:
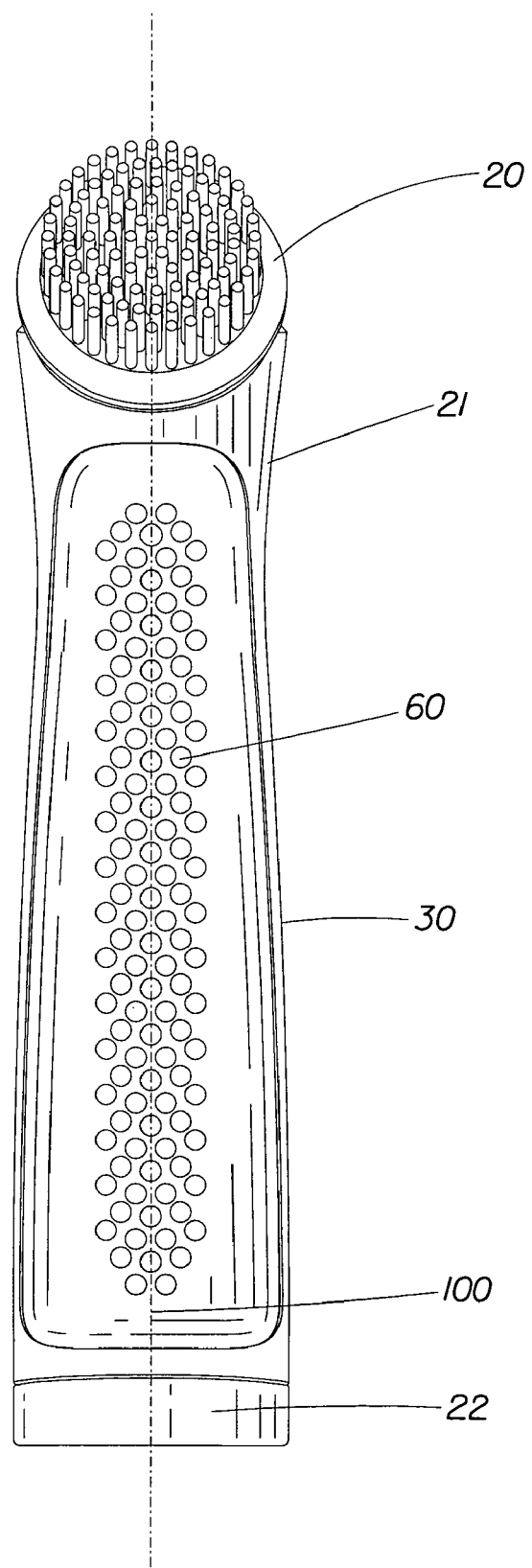
FIG. 1 is a front view of an motorized stain-removal brush made in accordance with the present invention, wherein the motorized stain-removal brush incorporates a rotating or oscillating coupling head.
Figure 2:
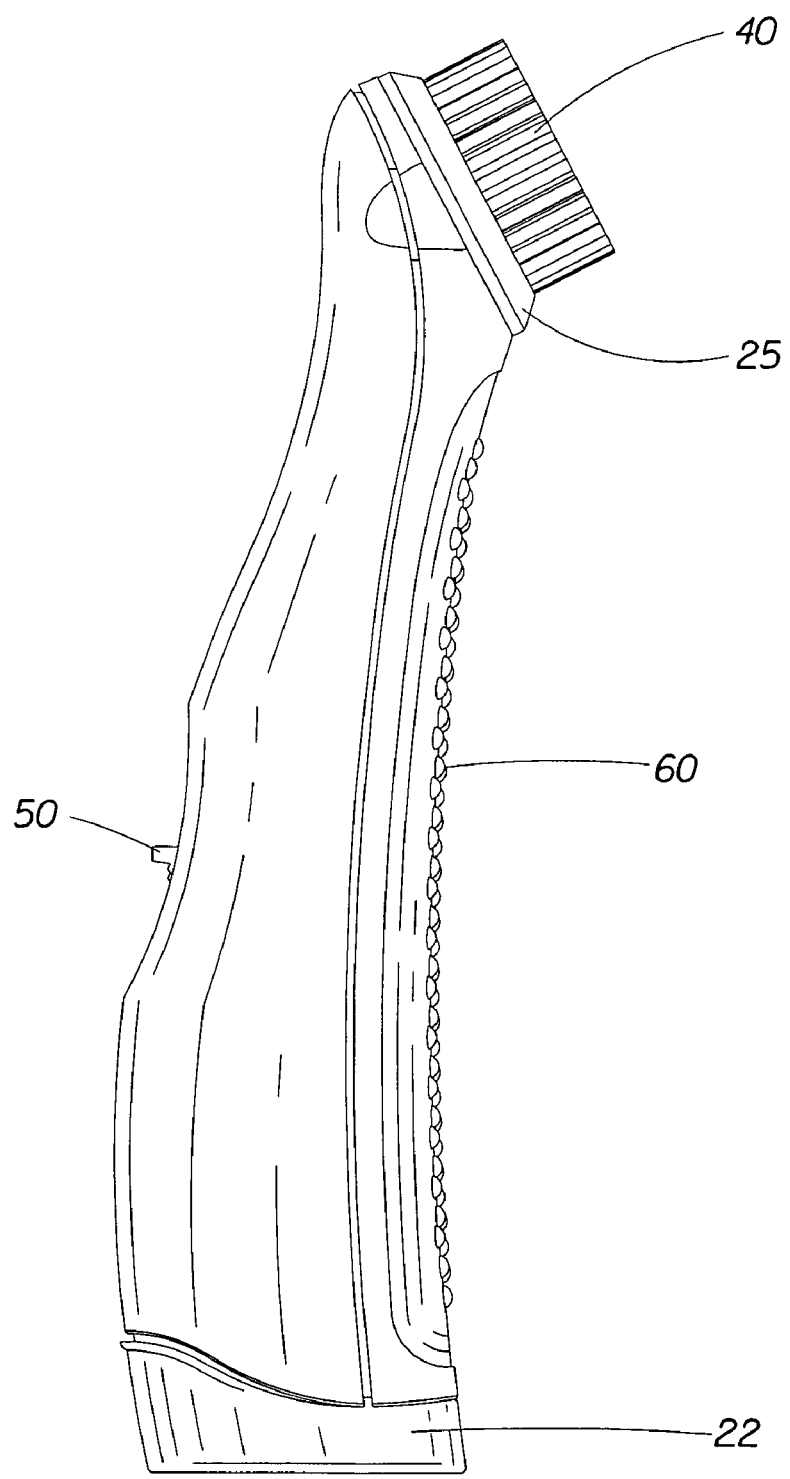
FIG. 2 is a side view of a motorized stain-removal brush of FIG. 1.
Figure 3:
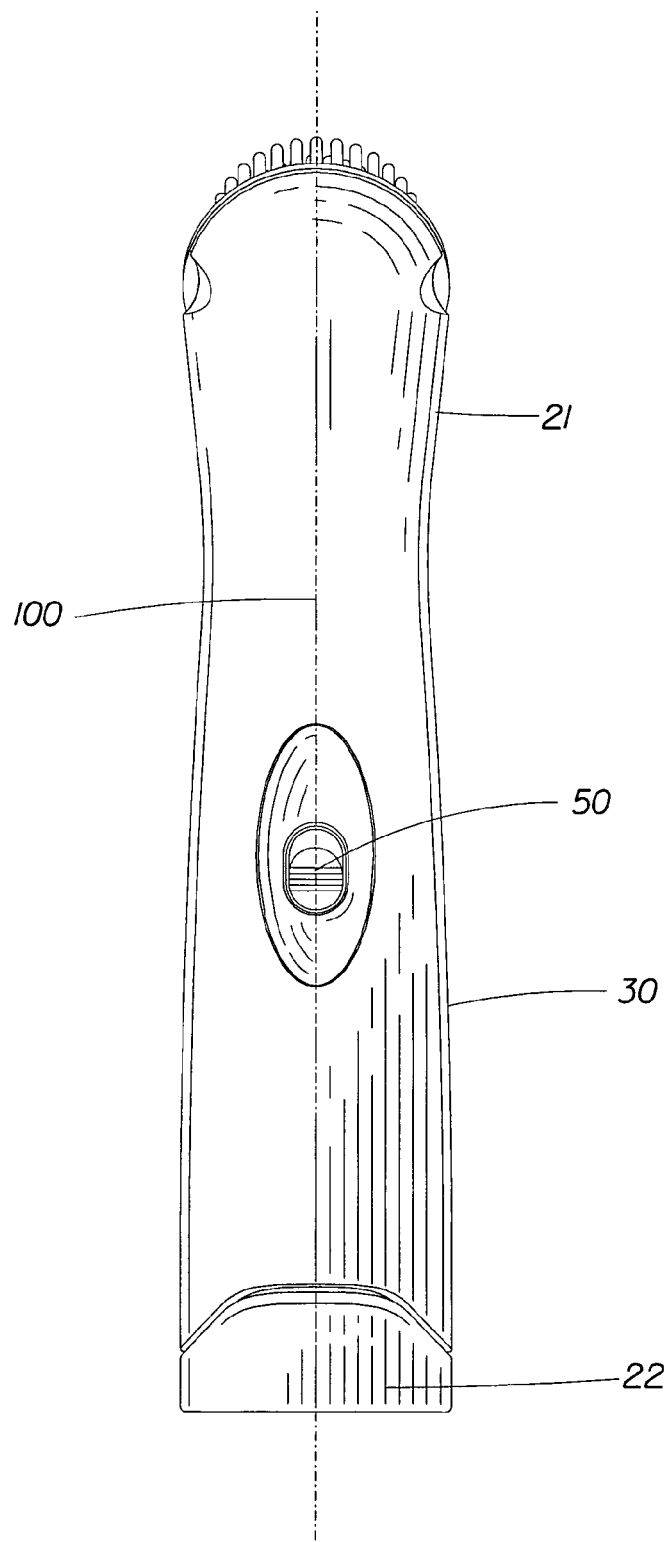
FIG. 3 is a rear view of the motorized stain-removal brush of FIG. 1.
Figure 4:
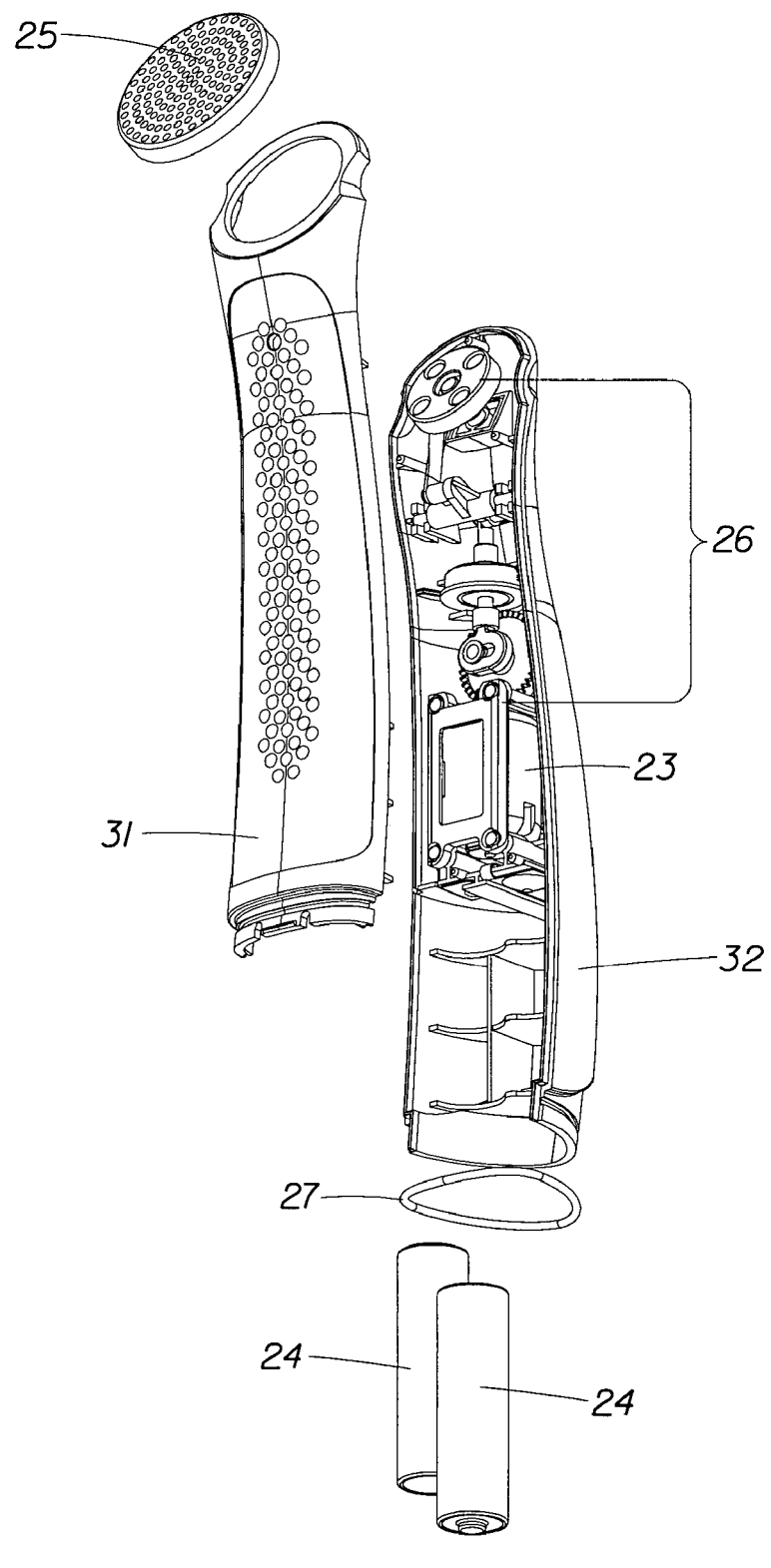
FIG. 4 is an exploded perspective view of an motorized stain-removal brush made in accordance with the present invention.
Figure 4:
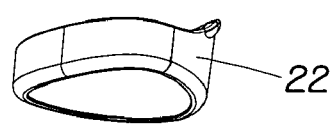

The present invention can be used in combination with electric stain-removal brushes and electric stain-removal brush heads that include shafts that rotate, oscillate, or reciprocate (as well as combinations thereof) to impart motion to the bristle holders. In addition, the present invention can be used in combination with electric stain-removal brushes and electric stain-removal brush heads where the shaft is operatively connected to the bristle holders. Referring to the Figures, some exemplary electric stain-removal brushes made in accordance with the present invention will now be described. These electric stain-removal brushes utilize a shaft that rotates or reciprocates. While these embodiments will be described with respect to the particular motor and shaft arrangement illustrated in FIG. 1 for purposes of simplicity and clarity, it will be appreciated that other motor and rotating (or oscillating) shaft arrangements can be substituted. For example, U.S. Pat. Nos. 5,617,603; 5,850,603; 5,974,615; 6,032,313; 5,732,432; 5,070,567; 5,170,525; 5,416,942; 3,588,936; 5,867,856; and 4,397,055, disclose other motor and rotating or oscillating shaft arrangements that might be suitable.

Turning to FIGS. 1 to 4, the electric stain-removal brush comprises a stain-removal brush head 20, a body or handle 30, and a neck 21 there between. The term "longitudinal" is intended to refer to a lengthwise feature of an element as seen from a top planar view thereof. For example, a longitudinal axis 100 is an axis passing through the longest dimension of an element, such as the head or a shaft. A longitudinal direction is a direction that generally corresponds to a longitudinal axis 100 but which may not line in the same plane as the longitudinal axis 100. For example, the longitudinal axes 100 of a shaft and a stain-removal brush head may not lie in the same plane but generally extend in the same direction from a front view. Similarly, a neck and head that are angled with respect to each other may not have longitudinal axes that lie in the same plane, but do have axes that extend in the same general longitudinal direction from a front view. The electric stain-removal brushes of the present invention typically have a cylindrical head.

The handle 30 is hollow and includes a front housing 31 and a rear housing assembly 32. The front housing 31 might contain a profiled surface or dimples 60 to provide a better handle grip. The handle also includes a motor 23, batteries 24, and a battery door 22 for powering the motor. A rechargeable power source can be substituted for the batteries. Also shown is a battery door seal ring 27. A bristle holder 25 is disposed at the end of the handle 30. While the bristle holder 25 is illustrated as circular in shape, other shapes can be utilized. The bristle holder 25 may be replaceable and includes a connection system to easily attach to the remote-most end of the linkage system 26. The remote-most end of the linkage system 26 is bent or offset from the longitudinal axis 100 of the motor shaft, allowing the bristle holder 25 to be angled and not in the same plane as the motor shaft. In other words, the bristle holder 25 oscillates about an axis wherein the axis has a slight inclination angle.

The stain-removal brush may be provided with a replaceable head or a non-replaceable head. Motorized stain-removal brushes made in accordance with the present invention will now be described. These motorized stain-removal brushes utilize a shaft that reciprocates. While these embodiments will be described with respect to the particular motor and shaft arrangement illustrated in FIGS. 5 and 6 for purposes of simplicity and clarity, it will be appreciated that other motor and reciprocating shaft arrangements can be substituted.

Figure 5:
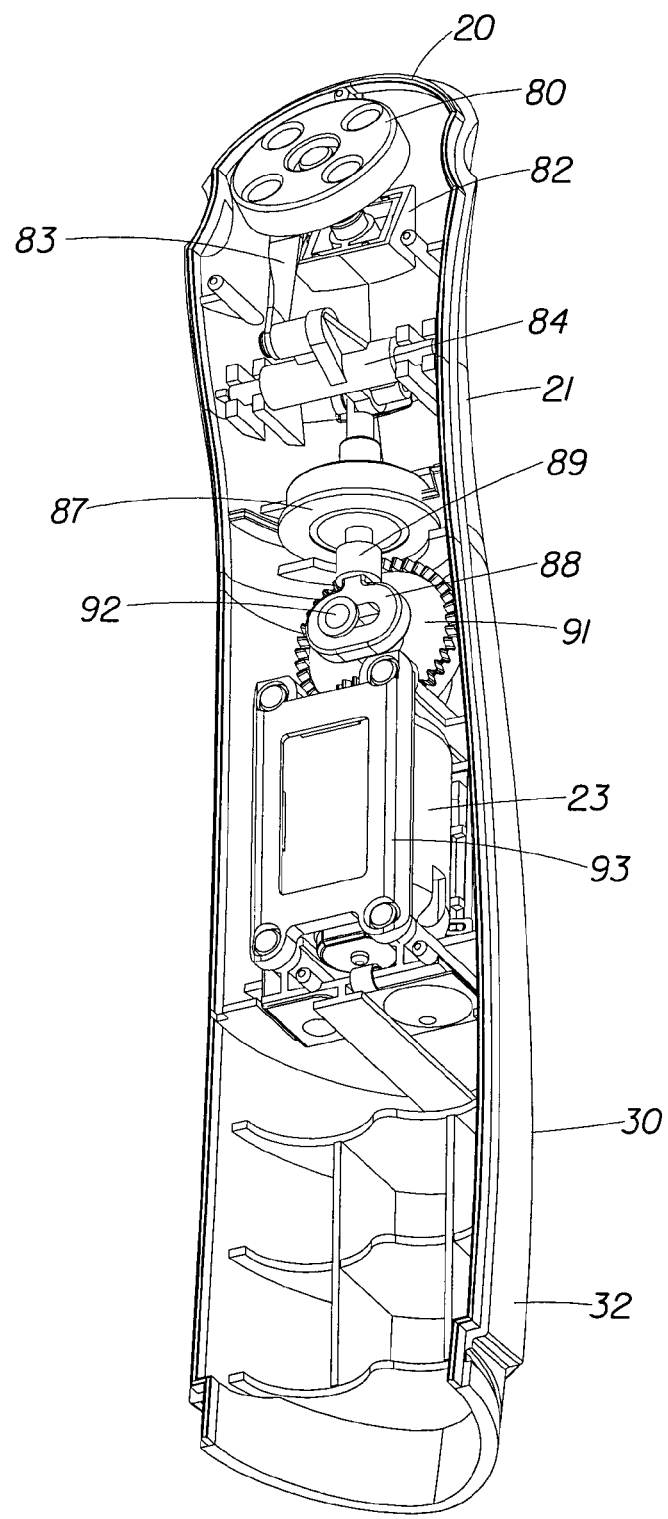
FIG. 5 is a perspective cutaway view of a linkage system suitable for use with the electric stain-removal brushes of FIGS. 1 to 4.
Figure 6:
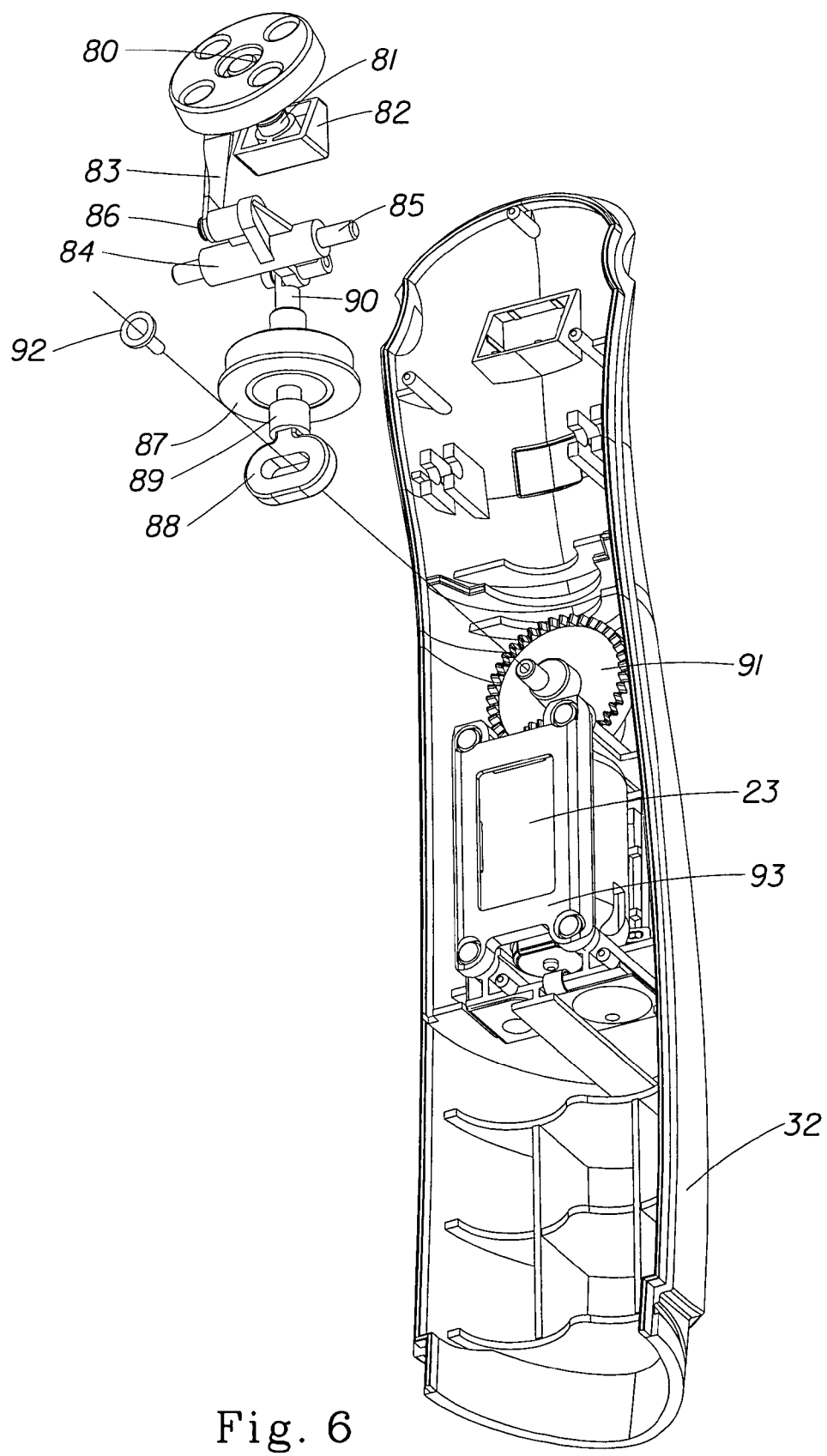
FIG. 6 is a perspective view showing an exploded view of a linkage system suitable for use with the motorized stain-removal brushes of FIGS. 1 to 4.

Turning to FIGS. 5 and 6, the motorized stain-removal brush comprises a stain-removal brush head 20, a body or handle 30, and an elongate neck 21 there between. The drive train, is comprised of the shafts and gears that transmit motion from the motor 23 to the coupling head 80 that connects with the replaceable bristle holder 25 (not shown) in a clip-on mode. While the coupling head 80 and the bristle holder are illustrated as circular in shape, other shapes can be utilized. The handle 30 is hollow. It consists of several compartments and includes a motor 23 and batteries (not shown) for powering the motor 23. The motor 23 is held in place in the rear housing 32 handle by the motor-holding plate 93. In this embodiment, the coupling head 80 only oscillates and does not reciprocate, translate, or perform any other non-rotational or oscillatory motion.

A first gear (not shown) is operatively connected to and powered by the motor 23. A second gear or crown gear 91 is operatively connected to the first gear. The rotational axis of the second gear 91 is approximately normal to the rotational axis of the first gear such that the teeth of the first gear mesh with teeth of the second gear 91, thus causing second gear 91 to rotate as the first gear rotates.

A T-link arm 88 is eccentrically and pivotably connected to the second gear 91 via a pin 92 or other fastening device. Due to the eccentric connection, the rotational motion of the second gear 91 is converted into a reciprocating motion of the T-link arm 88 moving the T-link shaft 89. The l-link 90 is fixedly secured, such as by a press fit into the T-link shaft 89 and linked to the V-link shaft 85 by pin 86 or other fastening device. The T-link shaft 89 is housed at least partially within the neck 21 and guided through a seal assembly 87. Referring to FIG. 6, the reciprocating T-link shaft 89 is connected at its terminal end to the V-link 84 which connects to the W-link 83 via pin 86 or other fastening device. The V-link 84 is supported by the V-link shaft 85. The terminal end of the W-link 83 connects to the coupling head 80. The W-link 83 is offset from the longitudinal axis of the T-link shaft 89 so that it is pinned adjacent the outer periphery of the coupling head 80. This offset arrangement converts the reciprocating motion of the W-link 83 into an oscillating motion of the coupling head 80. The coupling head 80 is connected to block 82 via pin 81. The brush head 20 receives block 82 in the rear housing 32.

Figure 7:
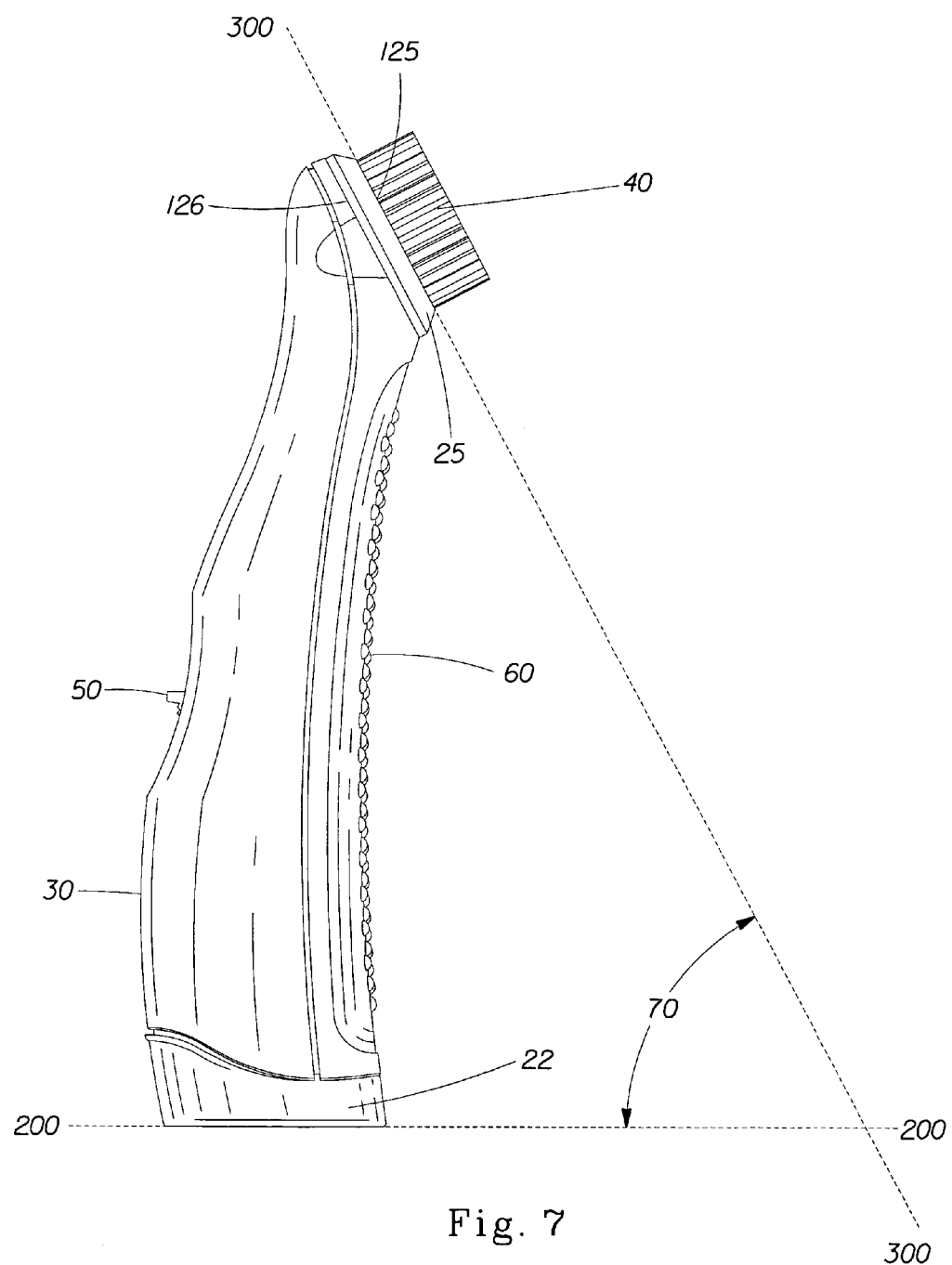
FIG. 7 is a side view which shows the cleaning efficiency angle of the stain-removal brush of FIGS. 1 to 4.

Referring to FIG. 7, a preferred embodiment of a stain-removal brush is the tilted or angled bristle holder 25 having a cleaning efficiency angle 70. The cleaning efficiency angle 70 preferably has a cleaning efficiency angle 70 of between about 0 and 100 degrees, more preferably between about 35 and 95 degrees and most preferably between about 40 and 90 degrees. The cleaning efficiency angle 70 is measured at the intersection of line 200-200 with line 300-300, wherein line 200-200 is measured at the intersection of the x-axis of the bottom of the handle 30 and wherein line 300-300 is measured at the y-axis of the top surface 125 of the bristle holder 25. Should the bottom of the handle 30 be a non-planar surface, the line 200-200 would be measured from the point tangent to the bottom-most point of handle 30. Should the top surface 125 of the bristle holder 25 be non-planar, the line 300-300 would be measured from the point tangent to the upper-most point on top surface 125.

The bristle holder 25, which is generally cylindrical in shape, has a preferred diameter of between about 10 and 50 millimeters and more preferably between about 20 and 40 millimeters. The distance between the top surface 125 of the bristle holder 25 and the bottom surface 126 of bristle holder 25 may be between about 2 and 15 millimeters. While embodiments of the present invention have been illustrated for simplicity with tufts of bristles that extend in a direction substantially perpendicular to the top surface of the bristle holders, it is contemplated that the bristles might be arranged differently to complement or further enhance the motions of the bristle holder. The bristle length is preferably between about 5 and 15 millimeters and more preferably between 7 and 12 millimeters. The bristle diameter is preferably between about 0.1 and 0.3 millimeters and more preferably between about 0.15 and 0.2 millimeters.

Figure 8:
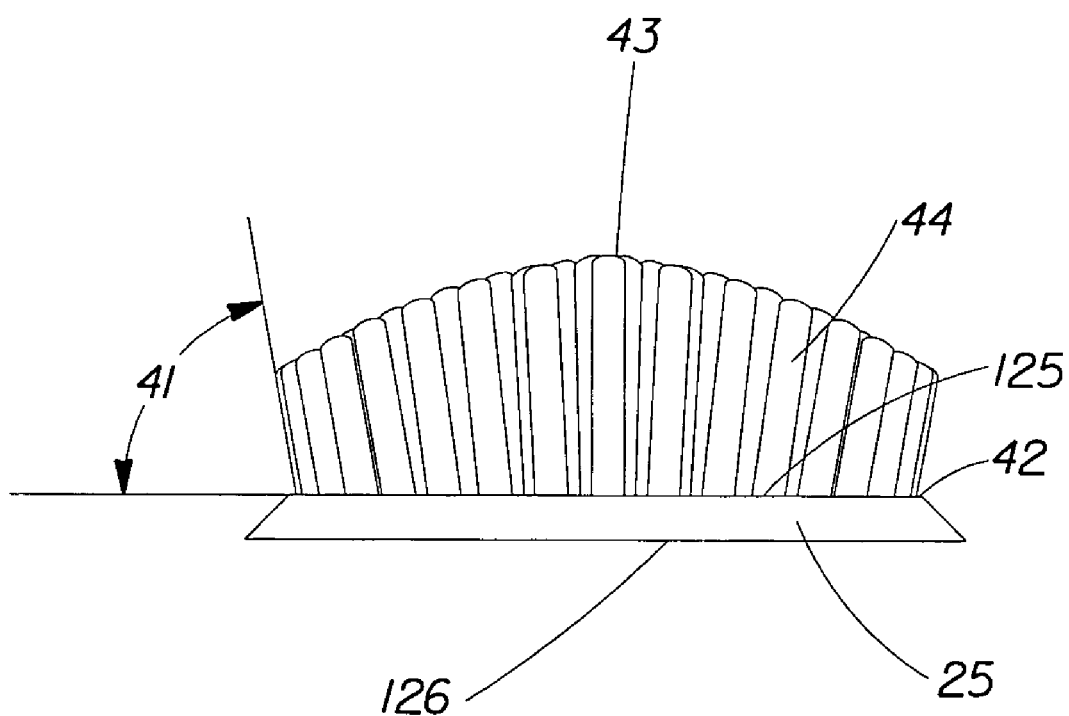
FIG. 8 is a side view of a stain-removal brush bristle tuft pattern suitable for use with the motorized stain-removal brushes of FIGS. 1 to 4.

While the electric stain-removal brushes of the present invention can be made with any combination of bristles, dimensions, combinations, angles and arrangements, a preferred arrangement is illustrated in FIG. 8. The bristle holder 25 has concentric rings of tufts. In one embodiment there are tall tufts 43 and shorter tufts 44 forming a dome shaped brush head. The difference in length between the tall tufts 43 and the shorter tufts 44 is between about 0.5 mm and 5 mm in one embodiment and between about 1 mm and 3 mm in other embodiment.

Figure 9:
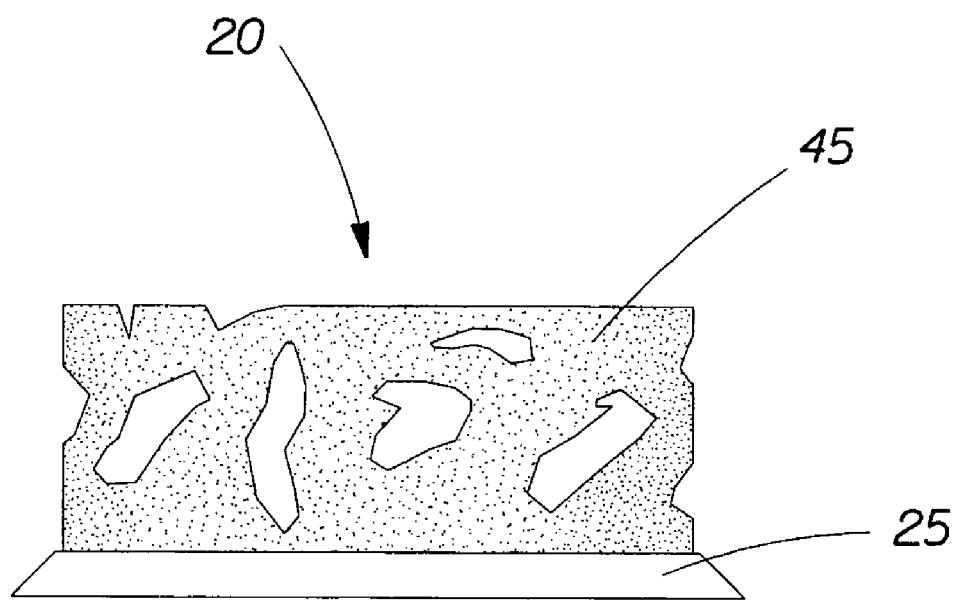
FIG. 9 is a side view of stain-removal brush head wherein a foam-like or sponge-like structure replaces the bristles suitable for use with the electric stain-removal brushes of FIGS. 1 to 4.

The bristles 40 can be provided with different characteristics, such as different heights (tall and short) as shown; and soft or firm. For example, soft bristles may be preferred for cleaning delicate fabrics (e.g., silk garments) and delicate hard surfaces (e.g., glass, plexiglass, compact discs, DVDs, gold plated surfaces, etc.). Alternatively, firmer bristles may be preferred for more rugged fabrics (e.g., denim, canvas, nylon, etc.) and most hard surfaces. Additionally, stiffer bristles typically require less force to be applied by the user, versus softer bristles. Less force applied by the user results in overall less stress on the user's fingers, hands, wrist arm and/or shoulder. In another embodiment, bristle tufts might be replaced in holder 25 by a sponge-like or foam structure 45 attached to the brush head 20 as shown in FIG. 9. Both bristles 40 and/or foam-like structures 45 may include different properties, non-limiting examples of which include antimicrobial properties and/or perfume ingredients.

In one non-limiting example the bristles may be made of Nylon 66 available from Tai Hing Nylon Filament Products Co., Ltd of Hong Kong. Examples of other suitable bristle materials include but are not limited to Nylon 6, Nylon 612, and polypropylene. The bristle diameter may be 6 mils and the bristle height may be 12 mm ±0.25 mm. The total area of the bristle head is approximately 93 $cm^2$. The bristle head may have a total of 94 tufts. Each tuft may consist of 34±4 bristles.

The bristle holder 25 oscillates at an angle of rotation between about 20 degrees and 45 degrees in one embodiment and between about 25 degrees and 35 degrees in another embodiment. The bristle holder has a peak oscillation frequency between about 1000 and about 10,000 cycles per minute in one embodiment and between about 2000 and 7000 cycles per minute in another embodiment. A cycle is one complete clockwise and counter-clockwise rotation (or vice versa) when the batteries are fully charged. It is contemplated that the oscillation frequency may drop outside of these ranges as the batteries are drained by use.

The stain-removal brush aspect of the invention has been described with reference to particular embodiments. Modifications and alterations will occur to others upon reading and understanding this specification. It is intended that all such modifications and alterations are included insofar as they come within the scope of the appended claims or equivalents thereof.

B. Method of Use

The present invention also encompasses a method of using the stain-removal brush to clean inanimate surfaces. In a preferred embodiment, the method comprises a) having the electric stain-removal brush of the present invention, b) putting a solution in contact with an inanimate surface; and c) employing the electric stain-removal brush to brush the solution on the inanimate surface.

The brush of the present invention is particularly useful for cleaning inanimate surfaces. For example, the stain-removal brush can be used alone or with additional laundry and stain pretreatment products (including but not limited to liquid and powder detergents, bleach, water, specialty pretreaters, and the like) to clean and remove stains from fabrics, particularly wearable fabrics. Fabrics include acrylic, cotton, lycra, polyester, rayon, spandex, washable silks with colorfast qualities, and wool, along with any blends of the above materials. The stain-removal brush can be used to apply products directly to the surface of the stain on the fabric via the bristles, or products can be directly applied to the stained fabric prior to using the device. Once the stain has been prepared and the operator has enabled the brush head 20 to rotate by actuating the power button 50, the stain-removal brush can be used to manually brush the surface of the stain on the fabric in any direction (circular, vertical, horizontal, diagonal, or any combination of the above). The stain-removal brush can also be used in the manner described above in a non-motorized or non-actuated mode.

Additional uses for the stain-removal brush include cleaning household fabrics such as upholstery, carpets, bedding, curtains, throw rugs, tablecloths, and other non-wearable fabrics in the same manner as listed above.

The stain-removal brush can also be used to clean inanimate hard surfaces, including those commonly found in a household (e.g., countertops, bathroom appliances, dishes, faucets, fixtures, floor baseboards, grout, kitchen appliances, shower doors, sinks, tile, toilets, tools, and tubs), shoe cleaning and polishing, car features (upholstery, cup holders, trim, detailing, car wheels, spokes) and jewelry.

Preferred hard surfaces include enamel surfaces. Herein, "enamel surface" means an inanimate surface being made of or coated with enamel. Herein "enamel" means titanium or zirconium white enamel or titanium or zirconium white powder enamel used as a coating for metal (e.g., steel) surfaces preferably to prevent corrosion of said metal surfaces. Enamel surfaces can typically be found in houses: e.g., in bathrooms or in kitchens, and include, e.g., bathrooms, fixtures and fittings sinks, showers, shower wash basins, tiles, tubs, and the like. Furthermore, cookware, dishes and the like may have an enamel surface. Enamel surfaces may also be found on household appliances which may be coated with enamel on their inside and/or outside surface including, but not limited to, automatic dryers, freezers, heating boiler, microwave ovens, conventional ovens, dishwashers refrigerators, washing machines, and so on. Further enamel surfaces may be found in industrial, architectural and the like applications. Examples of enamel surfaces found in said applications include enamel surfaces on or in architectural panels, chemical processing equipment, heat exchangers, hot water tanks, mechanical equipment, pipelines, pumps, reaction vessels, signs, silos, or tanks.

C. Self-instructing Article of Commerce

The present invention also encompasses articles of commerce comprising 1) the electric stain-removal brush of the present invention, and 2) a set of instructions directing the user in the method of the present invention for cleaning an inanimate surface.

In a preferred embodiment, the article of commerce comprises the stain-removal brush of the present invention in association with a set of instructions, wherein the instructions direct the user to follow the method of cleaning an inanimate surface described above. For example, in one embodiment, such instructions would direct the user to 1) put a solution in contact with the inanimate surface to be cleaned, and 2) employ the electric stain-removal brush to brush the solution on the inanimate surface.

Herein, "in association with", when referring to such instructions, means the instructions are either directly printed on the stain-removal brush; directly printed on the packaging for the stain-removal brush; printed on a label attached to the stain-removal brush; printed on a label attached to the packaging for the stain-removal brush; or presented in a different manner including, but not limited to, a brochure, print advertisement, electronic advertisement, broadcast or internet advertisements, and/or other media, so as to communicate the set of instructions to a consumer of the stain-removal brush.

The solutions employed in the present invention may be aqueous or non-aqueous. One non-limiting example of a non-aqueous solution is a lipophilic solution.

D. Aqueous Solution

As used herein, "aqueous solution" refers to a solution which contains water. The aqueous solution employed in the present invention may be any solution that facilitates the removal of a stain on an inanimate surface. In one embodiment, the aqueous solution comprises at least 10% water. In another embodiment the aqueous solution further comprises a surfactant.

Preferably, in embodiments involving the cleaning of fabrics, the aqueous solution is a liquid laundry detergent. In another embodiment for cleaning fabrics, the user may combine a granular laundry detergent with water to form a suitable aqueous solution.

Preferably, in embodiments involving the cleaning of hard surfaces, the aqueous solution is a liquid hard surface cleaner. In another embodiment for cleaning hard surfaces, the user may combine a granular hard surface cleaner with water to form a suitable aqueous solution.

In another embodiment, the aqueous solution further comprises a solvent. Solvents are particularly useful when cleaning a hard surface.

Additional non-limiting examples of aqueous solutions for use in the present invention may further comprise: ammonia, all-purpose cleaners, baking soda, bathroom/shower cleaners, bleach, car cleaners, and/or carpet cleaners.

In another embodiment, the aqueous solution further comprises particles. Such particles are particularly useful in facilitating mechanical disruption of a stain on the inanimate surface.

E. Lipophilic solution

The lipophilic solution employed in the present invention may be any non-aqueous solution that facilitates the removal of a stain on an inanimate surface and meets the requirements set forth in the Lipophilic Fluid Test (LF Test) as described below.

Qualification of Lipophilic Fluid—Lipophilic Fluid Test (LF Test)

Any non-aqueous fluid that is both capable of meeting known requirements for a stain removal fluid (e.g., flash point, etc.) and is capable of at least partially dissolving sebum, as indicated by the test method described below, is suitable as a lipophilic fluid herein. The ability of a particular material to remove sebum can be measured by any known technique. As a general guideline, perfluorobutylamine (Fluorinert FC-43®) on its own (with or without adjuncts) is a reference material that, by definition, is unsuitable as the lipophilic fluid herein (it is essentially a non-solvent) while cyclopentasiloxane (D5) dissolves sebum.

The following is the method for investigating and qualifying other materials, e.g., other low-viscosity, free-flowing silicones, for use as the lipophilic fluid. The method uses commercially available Crisco® canola oil, oleic acid (95% pure, available from Sigma Aldrich Co.) and squalene (99% pure, available from J. T. Baker) as model soils for sebum. The test materials should be substantially anhydrous and free from any added adjuncts, or other materials during evaluation.

Prepare three vials. Place 1.0 g of canola oil in the first; in a second vial place 1.0 g of the oleic acid (95%), and in a third and final vial place 1.0 g of the squalene (99%). To each vial add 1 g of the fluid to be tested for lipophilicity. Separately mix at room temperature and pressure each vial containing the lipophilic soil and the fluid to be tested for 20 seconds on a standard vortex mixer at maximum setting. Place vials on the bench and allow settling for 15 minutes at room temperature and pressure. If, upon standing, a single phase is formed in any of the vials containing lipophilic soils, then the fluid qualifies as suitable for use as a "lipophilic fluid" in accordance with the invention. However, if two or more separate layers are formed in all three vials, then the amount of fluid dissolved in the oil phase will need to be further determined before rejecting or accepting the fluid as qualified.

In such a case, with a syringe, carefully extract a 200 microliter sample from each layer in each vial. The syringe-extracted layer samples are placed in GC autosampler vials and subjected to conventional GC analysis after determining the retention time of calibration samples of each of the three models soils and the fluid being tested. If more than 1% of the test fluid by GC, preferably greater, is found to be present in any one of the layers which consists of the oleic acid, canola oil or squalene layer, then the test fluid is also qualified for use as a lipophilic fluid. If needed, the method can be further calibrated using heptacosafluorotributylamine, i.e., Fluorinert FC-43 (fail) and cyclopentasiloxane (pass).

A suitable GC is a Hewlett Packard Gas Chromatograph HP5890 Series II equipped with a split/splitless injector and FID. A suitable column used in determining the amount of lipophilic fluid present is a J&W Scientific capillary column DB-1 HT, 30 meter, 0.25 mm id, 0.1 µm film thickness cat#1221131. The GC is suitably operated under the following conditions:

Carrier Gas: Hydrogen

Column Head Pressure: 9 psi

Flows: Column Flow@~1.5 ml/min.

Split Vent@~250-500 ml/min.

Septum Purge@1 ml/min.

Injection: HP7673 Autosampler, 10 ul syringe, 1 ul injection

Injector Temperature: 350° C.

Detector Temperature: 380° C.

Oven Temperature Program: initial 60° C., hold 1 min. rate 25° C./min. final 380° C. hold 30 min.

Preferred lipophilic fluids suitable for use herein can further be qualified for use on the basis of having an excellent garment care profile. Garment care profile testing is well known in the art and involves testing a fluid to be qualified using a wide range of garment or fabric article components, including fabrics, threads and elastics used in seams, etc., and a range of buttons. Preferred lipophilic fluids for use herein have an excellent garment care profile, for example they have a good shrinkage or fabric puckering profile and do not appreciably damage plastic buttons.

For purposes of garment care testing or other qualification, e.g., flammability, a lipophilic fluid for use in the lipophilic fluid can be present in a mixture, e.g., with water, at approximately the ratio to be used in the final lipophilic fluid which will come into contact with fabric articles. Certain materials, which remove sebum, qualify for use as lipophilic fluids; for example, ethyl lactates can be quite objectionable in their tendency to dissolve buttons, and if such a material is to be used in the lipophilic fluid, it will be formulated with water and/or other solvents such that the overall mix is not substantially damaging to buttons. Other lipophilic fluids, D5 for example, meet the garment care requirements commendably. Some suitable lipophilic fluids may be found in granted U.S. Pat. Nos., 5,865,852; 5,942,007; 6,042,617; 6,042,618; 6,056,789; 6,059,845; and 6,063,135.

Lipophilic solvents can include linear and cyclic polysiloxanes, hydrocarbons and chlorinated hydrocarbons. More preferred are the linear and cyclic polysiloxanes and, hydrocarbons of the glycol ether, acetate ester, lactate ester families. Preferred lipophilic solvents include cyclic siloxanes having a boiling point at 760 mm Hg. of below about 250° C. Specifically preferred cyclic siloxanes for use in this invention are octamethylcyclotetrasiloxane, decamethylcyclopentasiloxane, and dodecamethylcyclohexasiloxane. It should be understood that useful cyclic siloxane mixtures might contain, in addition to the preferred cyclic siloxanes, minor amounts of other cyclic siloxanes including hexamethylcyclotrisiloxane or higher cyclics such as tetradecamethylcycloheptasiloxane. Generally the amount of these other cyclic siloxanes in useful cyclic siloxane mixtures will be less than about 10 percent based on the total weight of the mixture.

F. Absorbent Stain Receiver Article

In another embodiment, the stain-removal brush and cleaning solution is used in combination with an Absorbent Stain Receiver Article ("ASRA"). The ASRA herein can comprise any of a number of absorbent structures which provide a capillary pressure difference through their thickness (Z-direction). When designing the ASRA for use in the spot removal process herein, the following matters are taken into consideration. First, the cleaning solution only removes the soil from the fibers of the fabric even with agitation. If the cleaning solution which carries the soil is allowed to remain in the fabric, the soil will be redeposited on the fabric as the cleaning solution dries. The more complete the removal of cleaning solution from the fabric, the more complete will be the removal of soil.

Second, the fabric being treated is, itself, basically a fibrous absorbent structure which holds liquid (i.e., the cleaning solution) in capillaries between the fibers. While some liquid may be absorbed into the fibers, most of the liquid will be held in interfiber capillaries (this includes capillaries between filaments twisted into a thread). Liquid held in the fabric may be removed by contacting it with another absorbent structure such as the ASRA, herein. In this process, liquid is transferred from the capillaries of the fabric to the capillaries of the ASRA.

Third, liquid is held in capillaries by capillary pressure. Capillary pressure (Pc) is generally described by the following equation:

$$Pc = (2 \times G \times Cos\, A)/R$$

where
  $G$ = the surface tension of the liquid
  $A$ = the contact angle between the liquid and the capillary wall
  $R$ = the radius of the capillary Accordingly, capillary pressure is highest in capillaries which have a low contact angle and a small radius. Liquid is held most tightly by high capillary pressure and will move from areas of low capillary pressure to areas of high capillary pressure. Hence, in the subject ASRA which provides a capillary pressure difference through its thickness, liquid will move from low capillary pressure areas to high capillary pressure areas. Capillary pressure can be measured using a variety of techniques, but will employ the liquid cleaning composition as the test liquid.

In reality, most absorbent materials are complex structures comprised of a range of capillary sizes and contact angles. For this discussion, the capillary pressure of a material or capillary pressure zone within a material is defined as the volumetric weighted average of the range of pressures found within that material or zone.

For purposes of illustration, in circumstances wherein a soiled fabric saturated with cleaning solution is in liquid communication contact with two stacked, identical layers of homogeneous absorbent material, such as a paper towel, solution and soil would readily transfer from the fabric to the towel until the capillary pressure is approximately equal in the two materials. At equilibrium a certain amount of solution and soil will remain in the fabric. The exact amount will depend on the basis weight and capillary pressure characteristics of the fabric and towel. A reduced amount of residual solution and soil in the fabric, and therefore better cleaning, would result from replacing the bottom layer (layer not in direct contact with the fabric) of towel with an absorbent layer of capillary pressure higher than that of the towel. By virtue of its higher capillary pressure this absorbent layer will cause more solution to transfer from the low capillary pressure top towel layer to the high capillary pressure absorbent layer which in turn causes more solution to transfer from the fabric to the top towel layer. The result is better cleaning due to less residual solution and soil remaining in the fabric.

This type of multi-layer system is also beneficial when Z-directional pressure is applied to the wetted stained fabric and ASRA. This pressure compresses the various materials, thereby lowering their void volume and liquid absorption capacity (increasing the % saturation of the materials). This can cause liquid to be squeezed out. The layered structure allows for free liquid to be absorbed by the lower layer, i.e., the one furthest away from the fabric. This lessens the reabsorption of liquid by the fabric. This is especially true if the bottom layer (layer of highest capillary pressure) is also relatively incompressible (retains a higher percentage of its void volume under pressure) compared to the top layer (layer of lower capillary pressure). In this case it may be desirable for the top layer to be resiliently compressible so as to express liquid under pressure which can be absorbed by the bottom layer.

Thus the ASRA can comprise two or more relatively distinct layers which differ in capillary pressure. As can be seen from the capillary pressure equation, a difference in capillary pressure can be achieved by varying the capillary size or the contact angle between the cleaning solution and the ASRA. Both factors can be controlled by the composition of the ASRA. The contact angle portion of the equation can also be affected by chemical treatment of the ASRA with, for example, a surfactant to lower the contact angle or a water repellent material such as silicone to increase contact angle.

The effectiveness of an ASRA comprising multiple layers of differing capillary pressure can be enhanced by locating most of the total absorbent capacity in the high capillary pressure portion. The top fabric facing layer need only be thick enough to insulate the fabric from the liquid held in the bottom layer.

The effectiveness of the layered ASRA can be further enhanced by selecting the low capillary pressure portion to have a capillary pressure higher than that of the fabric being treated.

In an ASRA comprised of two or more layers differing in capillary pressure, the pattern of capillary pressure change can be characterized as "stepped". Through the thickness of the ASRA there is a sharp change or step in capillary pressure at the layer interfaces. It will be appreciated that the ASRA herein need not comprise multiple distinct layers, but rather can comprise a single layer structure with a relatively continuous capillary size gradient through its thickness.

Fibers—The ASRA can be made from a variety of materials including fibrous absorbents and foams. Useful fibrous absorbents include nonwoven fabrics (carded, hydroentangled, thermal bonded, latex bonded, meltblown, spun, etc.), thermal bonded airlaid nonwovens ("TBAL"), latex bonded airlaid nonwovens ("LBAL"), multi-bonded airlaid nonwovens ("MBAL" combined latex and thermal bonded), wet laid paper, woven fabrics, knitted fabrics or combination of materials (i.e., top layer of a carded nonwoven, and a bottom layer of wet laid paper). These fibrous absorbents can be manufactured using a wide variety of fibers including both natural and synthetic fibers. Useful fibers include wood pulp, rayon, cotton, cotton linters, polyester, polyethylene, polypropylene, acrylic, nylon, multi-component binder fibers, etc. Multiple fiber types can be blended together to make useful materials. Useful foam materials include polyurethane foams and high internal phase emulsion foams. The critical factor is to have a difference in capillary pressure within the thickness of the ASRA. A broad range of fiber sizes can be employed. A typical, but non-limiting range of diameters is from about 0.5 micrometers to about 60 micrometers. For meltblown, the preferred fibers are less than about 10 micrometers. Typical spun-bond and synthetic staple fibers range in diameter from about 14 to about 60 micrometers. In general, one selects smaller diameter fibers for the high capillary pressure layer and higher diameters for low capillary pressure. Fiber length can depend on the forming process that is being used and the desired capillary pressure. Spun-bonds comprise a substantially continuous fiber. For air-laid fibers, 4-6 mm is typical. For carded fibers the range is typically 25-100 mm. In addition, it has now been found that enriching the upper layer in bicomponent fibers decreases linting during use. Cleaning can also be enhanced by making the top layer rich in synthetic (e.g., bicomponent) fibers due to their lipophilic nature which aids in the removal of oily stains from the fabric being treated.

Absorbent gelling materials ("AGM") such as those sometimes referred to in the diaper art as 'supersorbers' can be added to either or both layers of the receiver or as a discrete layer between the fiber layers or on the back of the bottom layer of the ASRA. Functionally, the AGM provides additional liquid absorption capacity and serves to drain the capillaries in the ASRA structure which helps to maintain the capillary pressure gradient as liquid is absorbed.

In light of the foregoing considerations, the ASRA herein can be defined as an absorbent structure which has a capillary pressure difference through its thickness (Z-direction). In a typical, but non-limiting mode, this can be achieved by having relatively larger capillaries (for example 50-100 micrometers radius) in the upper, liquid-receiving portion of the ASRA which is placed in contact with the fabric being treated. The lower, liquid-storage portion having relatively smaller capillaries (for example 5-30 micrometers radius). Irrespective of the size employed, it is desirable that the difference in average capillary pressure between the two layers be large enough that the overlap in capillary pressure range between the two layers is minimized.

Basis Weight—The basis weight of the ASRA can vary depending on the amount of cleaning solution which must be absorbed. A preferred 127 mm×127 mm receiver absorbs about 10-50 grams of water. Since very little liquid is used in the typical stain removal process, much less capacity is actually required. A typical TBAL ASRA pad weighs about 4-6 grams. A useful range is therefore about 1 gram to about 7 grams. A variety of sizes can be used, e.g., 90 mm×140 mm.

Size—The preferred size of the ASRA is about 127 mm×127 mm, but other sizes can be used, e.g., 90 mm×140 mm. The shape can also be varied.

Thickness—The overall thickness of the preferred ASRA is about 3 mm (120 mils) but can be varied widely. The low end may be limited by the desire to provide absorbency impression. A reasonable range is 25 mils to 200 mils.

Lint Control Binder Spray—The ASRA is preferably dust free. Some materials are naturally dust free (synthetic nonwoven fabrics). Some, generally cellulose containing materials, can be dusty because not all the fibers are bonded. Dust can be reduced by bonding substantially all the fibers which reside on or near the surface of the ASRA which contacts the fabric being treated. This can be accomplished by applying resins such as latex, starch, polyvinyl alcohol or the like. Cold or hot crimping, sonic bonding, heat bonding and/or stitching may also be used along all edges of the receiver to further reduce Tinting tendency.

Backing Sheet—The ASRA is generally sufficiently robust that it can be used as-is. However, in order to prevent strikethrough of the liquid onto the table top or other treatment surface selected by the user, it is preferred to affix a liquid-impermeable barrier sheet to the bottom-most surface of the lower layer. This backing sheet also improves the integrity of the overall article. The bottom-most layer can be extrusion coated with an 0.5-2.0 mil, preferably 1.0 mil, layer of polyethylene or polypropylene film using conventional procedures. A film layer could also be adhesively or thermally laminated to the bottom layer. The film layer is designed to be a pinhole-free barrier to prevent any undesired leakage of the cleaning composition beyond the receiver. This backing sheet can be printed with usage instruction, embossed and/or decorated, according to the desires of the formulator. The ASRA is intended for use outside the dryer. However, since the receiver may inadvertently be placed in the dryer and subjected to high temperatures, it is preferred that the backing sheet be made of a heat resistant film such as polypropylene or nylon.

Colors—White is the preferred color for the ASRA as it allows the user to observe transfer of the stain from the fabric to the receiver. However, there is no functional limit to the choice of color. The backing sheet can optionally be a contrasting color.

Embossing—The ASRA can also be embossed with any desired pattern or logo.

Manufacture—A typical, but non-limiting, embodiment of the ASRA herein is a TBAL material which consists of an upper, low capillary pressure layer which is placed in liquid communication contact with the fabric being treated and a bottom high capillary pressure layer. The ASRA can be conveniently manufactured using procedures known in the art for manufacturing TBAL materials; see U.S. Pat. No. 4,640,810. As an overall proposition, TBAL manufacturing processes typically comprise laying-down a web of absorbent fibers, such as relatively short (2-4 mm) wood pulp fibers, in which are commingled relatively long (4-6 mm) bi-component fibers. The sheath of the bicomponent fiber melts with the application of heat to achieve thermal bonding. The bi-component fibers intermingled throughout the wood pulp fibers thereby act to 'glue' the entire mat together. Both layers in one embodiment of the ASRA herein can be a homogeneous blend of wood pulp fibers and bi-component thermal bonding fibers. In a more preferred embodiment, the top layer is 100% concentric bi-component fiber comprising 50:50 (wt.) polyethylene (PE) and polypropylene (PP) comprising a PP core enrobed in an outer sheath of PE. The gradient is achieved by providing a higher proportion of bicomponent bonding fibers in the top layer compared to the bottom layer. Using a TBAL process as described in U.S. Pat. No. 4,640,810, the top, low capillary pressure layer is formed by a first forming station from 100% bicomponent fiber (AL-Thermal-C, 1.7 dtex, 6 mm long available from Danaklon a/s). Basis weight of this all-bicomponent top layer is approximately 30 gsm (grams/meter$^2$). The bottom, high capillary pressure layer is formed upon the top layer by second and third forming stations from a fiber blend consisting of approximately 72% wood pulp (Flint River Fluff available from Weyerhaeuser Co.) and approximately 28% bi-component binder fiber. Basis weight of this bottom layer is approximately 270 gsm. Each of the second and third forming station deposits approximately half of the total weight of the bottom layer. The two layers are then calendered to provide a final combined thickness of approximately 3 mm. Subsequently, a 1.0 mil coating of polypropylene is extrusion coated onto the exposed surface of the bottom layer. Individual receivers are cut to 127 mm×127 mm size. In one optional mode, since the material will be wound into a roll before applying the back sheet, a binder (e.g., latex—Airflex 124 available from Air Products) can be applied to the exposed surface of the lower layer prior to thermal bonding to prevent transfer of dust to the top all-bicomponent layer. Alternatively, a non-linting sheet can be placed on the ASRA during roll-up to prevent linting due to contact between the surfaces.

The composition and basis weights of the layers can be varied while still providing an ASRA with the desired capillary pressure gradient and cleaning performance.

G. Method of Measuring Cleaning Efficiency Angle

Figure 10:
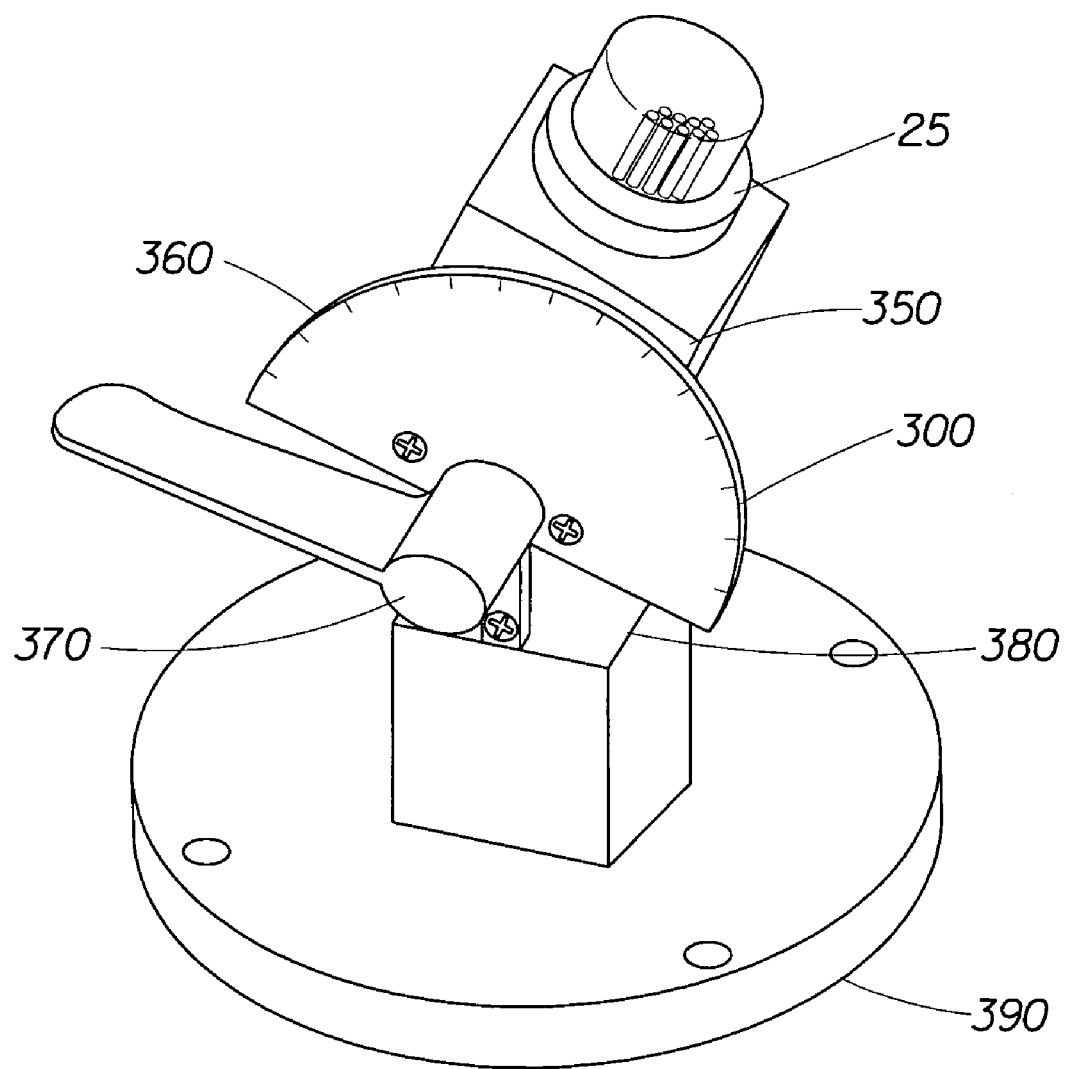
FIG. 10 is a perspective view of a device which can be used in conjunction with a tensile tester to measure cleaning efficiency angle.

This provides a method which may be used to measure the cleaning efficiency angle. An instrument for measuring tensile strength may be used. A non-limiting example of a suitable instrument is an Instron Model #8511 manufactured by Instron, Inc. of Canton, Mass. Referring to FIG. 10, the bristle holder 25 is mounted onto a plastic block 300. A protractor 350 having angular degree gradations is mounted onto the plastic block *300. The protractor 350 and plastic block 300 are attached to one another with pivot arm 370. The protractor 350, plastic block 300, and pivot arm 370 are attached to a base 380. The base 380 is attached to mounting bracket 390. The mounting bracket is available from Instron, Inc. The protractor 350 and plastic block 300 may be pivoted in relation to base 380 and mounting bracket 390 to the desired angle. The mounting bracket 390 is then mounted onto the tensile tester such that the center point of the bristle holder 25 is aligned with the load cell center line. The force reading from the load cell is set to the 200 pound range. The displacement rate is 0.5 inches per minute. Rest at full displacement is 0.5 seconds.

EXAMPLE

The method described above was used to measure cleaning efficiency angle. An Instron Model #8511 was used utilizing the Instron displacement program referred to as "trapezoid". A force reading from the Instron load cell was 200 pound range. The force and displacement were monitored at Nicolet Pro 20 o-scope. For each test increment the angle of brush engagement was set. Tests were run at 2.5 degree increments both to the right and to the left. Top dynamic faceplate is manually lowered from non-engagement position (zero) to point of full brush bristle face engagement. This is total test displacement. This point becomes test stop, rest and return. Dynamic faceplate is returned to zero position. Full brush engagement is experienced when all bristles actually engage the top faceplate. Nicolet is calibrated against a 5 pound weight and programmed to provide displacement in inches (channel 1) and force in pounds (channel 2). Nicolet is triggered at displacement curve. Nicolet curves are against time in seconds. At test start: dynamic face plate lowers to engage brush at 0.5 inches per second to point of full brush face engagement. Rest for 0.5 seconds. Returns to zero displacement point at 0.5 inches per second. This cycle is repeated at least once to insure repeatability. At the Nicolet: engagement point between dynamic faceplate and first bristle plain is determined. This point and total test displacement difference determines the full bristle engagement displacement. At the Nicolet: engagement point at first bristle contact (zero force) and total test displacement determines reported force at full bristle engagement. This is a dynamic force reading. The static force reading occurs at the 0.5 second rest. The static force reading will be slightly higher than the dynamic force reading.

The aspects and embodiments of the present invention set forth in this document have many advantages. For example, the present invention can provide improved cleaning and/or faster cleaning results on inanimate surfaces; as well as reduced fatigue on the user's fingers, hands, arms and/or shoulders.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. All documents cited herein are in relevant part, incorporated by reference. The citation of any document is not to be construed as an admission that it is prior art with respect to the present invention.

What is claimed is:

1. A method of cleaning an inanimate surface comprising:
   a) providing a motorized stain-removal brush having a cleaning efficiency angle of from between about 0 degrees to 100 degrees, wherein the motorized stain-removal brush comprises:
      i) a handle having a motor disposed therein;
      ii) a head having a longitudinal axis;
      iii) a neck disposed between the handle and the head;
      iv) a tilted bristle holder associated with the head which oscillates or rotates;
      v) a set of bristles associated with the bristle holder wherein the motor is operatively connected to bristle holder;
      vi) a shaft at least partially disposed within the neck, the shaft being operatively connected to the motor and to the bristle holder, wherein the terminal end of the shaft disposed in the neck does not lie in the same plane as the motor shaft disposed in the handle;
   b) putting a solution in contact with an inanimate surface; and
   c) contacting the motorized stain-removal brush to the inanimate surface so as to brush the solution on the inanimate surface.

2. The method of claim 1, wherein the tilted bristle holder oscillates at a frequency of between about 1000 and 10,000 cycles per minutes.

3. The method of claim 1, wherein the bristle holder has a circular shape with a diameter of between about 10 and 50 mm.

4. The method of claim 1, wherein the bristles have a length of between about 5 and 15 mm.

5. The method of claim 1, wherein the bristles have a diameter of between about 0.1 and 0.3 mm.

6. The method of claim 1, wherein the solution is an aqueous solution.

7. The method of claim 6 wherein the aqueous solution is first applied to the bristles, and then placed in contact with the inanimate surface.

8. The method of claim 6, wherein the solution further comprises a surfactant.

9. The method of claim 1, wherein the solution is a lipophilic fluid.

10. The method of claim 9 wherein the lipophilic solution is first applied to the bristles, and then placed in contact with the inanimate surface.

11. The method of claim 9 wherein the lipophilic solution further comprises a surfactant.

12. The method of claim 1, wherein the shaft reciprocates.

13. The method of claim 1, wherein the shaft comprises a V-link.

14. The method of claim 1, wherein the terminal end of the shaft comprises a W-link.

15. The method of claim 1 wherein the bristles tufts have different lengths.

16. The method of claim 1 wherein the bristle bolder has a sloped base.

17. A method of cleaning an inanimate surface comprising:
   a) providing an electric stain-removal brush, wherein the electric stain-removal brush has a cleaning efficiency angle of between about 0 degrees and 100 degrees and wherein the stain removal brush comprises:
      i) a handle having a motor disposed therein;
      ii) a head having a longitudinal axis;
      iii) a neck disposed between the handle and the head;
      iv) a tilted bristle holder associated with the head which oscillates or rotates;
      v) a set of bristles associated with the bristle holder wherein the motor is operatively connected to bristle holder;
      vi) a shaft at least partially disposed within the neck, the shaft being operatively connected to the motor and to the bristle holder, wherein the terminal end of the shaft disposed in the neck does not lie in the same plane as the motor shaft disposed in the handle;
   b) providing an absorbent stain receiver article which contacts the inanimate surface;
   c) putting a solution in contact with the inanimate surface;
   d) contacting the electric stain-removal brush to brush the solution on the inanimate surface; and
   e) contacting the inanimate surface treated with the solution with the absorbent stain receiver article.

18. An article of commerce comprising
   a) a motorized stain-removal brush, wherein the motorized stain-removal brush comprises
      i) a handle having a motor disposed therein;
      ii) a head having a longitudinal axis;
      iii) a neck disposed between the handle and the head;
      iv) a bristle holder associated with the head which oscillates or rotates and wherein the motorized stain-removal brush has a cleaning efficiency angle of between about 0 and 100 degrees; and
      v) a set of bristles or a foam structure associated with the bristle holder; wherein the motor is operatively connected to the bristle holder; and vi) a shaft at least partially disposed within the neck, the shaft being operatively connected to the motor and to the bristle holder, wherein the terminal end of the shaft disposed in the neck does not lie in the same plane as the motor shaft disposed in the handle.

19. The article of claim 18 further comprising a set of instructions in association with the motorized stain-removal brush, wherein the instructions direct a user of the motorized stain-removal brush to
   i) put a solution in contact with the inanimate surface, and
   ii) employ the motorized stain-removal brush to brush the solution on the inanimate surface.

20. The article of commerce of claim 18 wherein the bristle holder is tilted.

21. The article of commerce of claim 18 wherein the bristle holder oscillates.

22. The article of commerce of claim 18 wherein the motorized stain-removal brush has a cleaning efficiency angle of between about 35 and 95 degrees.

* * * * *